(12) United States Patent  (10) Patent No.: US 12,179,002 B2
Abrams et al.                (45) Date of Patent:     Dec. 31, 2024

(54) SYRINGE AND GASKET SYSTEMS

(71) Applicant: SiO2 Medical Products, LLC, Auburn, AL (US)

(72) Inventors: Robert S. Abrams, Auburn, AL (US); Kenneth Wade Kelly, Auburn, AL (US); Ahmad Taha, Auburn, AL (US); Benjamin Hunt, Auburn, AL (US); Brian Russell Lilly, Auburn, AL (US); Ralf Kibele, Auburn, AL (US)

(73) Assignee: SiO2 Medical Products, LLC, Auburn, AL (US)

( * ) Notice: Subject to any disclaimer, the term of this patent is extended or adjusted under 35 U.S.C. 154(b) by 697 days.

(21) Appl. No.: 17/311,540

(22) PCT Filed: Dec. 6, 2019

(86) PCT No.: PCT/US2019/065099
§ 371 (c)(1),
(2) Date: Jun. 7, 2021

(87) PCT Pub. No.: WO2020/118275
PCT Pub. Date: Jun. 11, 2020

(65) Prior Publication Data
US 2022/0040412 A1    Feb. 10, 2022

Related U.S. Application Data

(60) Provisional application No. 62/825,166, filed on Mar. 28, 2019, provisional application No. 62/789,366, (Continued)

(51) Int. Cl.
A61M 5/31     (2006.01)
A61M 5/315    (2006.01)
(Continued)

(52) U.S. Cl.
CPC ..... A61M 5/31513 (2013.01); B23K 26/0823 (2013.01); B23K 26/364 (2015.10);
(Continued)

(58) Field of Classification Search
CPC ...... A61M 5/31513; A61M 2005/3101; A61M 2205/0238; A61M 2207/00; B29C 67/0048
See application file for complete search history.

(56) References Cited

U.S. PATENT DOCUMENTS 10,173,013 B2    1/2019  Kaneko et al.
2016/0243308 A1  8/2016  Giraud et al.
(Continued)

FOREIGN PATENT DOCUMENTS

EP    3058975    8/2016
EP    3409311    12/2018
(Continued)

Primary Examiner — Robert B Davis
(74) Attorney, Agent, or Firm — HALEY GUILIANO LLP; James F. Haley, Jr.

(57) ABSTRACT

A process for producing gaskets with an improved channel for use in matched syringe and plunger systems, preferably prefilled plastic syringe systems. In particular, an improved process for making and inspecting continuous channels in a gasket film by laser treatment. The gaskets are useful in matched syringe and plunger systems with high and consistent container closure integrity (CCI), and consistent break loose and glide forces over time, and sealability.

18 Claims, 4 Drawing Sheets

Related U.S. Application Data filed on Jan. 7, 2019, provisional application No. 62/788,168, filed on Jan. 4, 2019, provisional application No. 62/776,958, filed on Dec. 7, 2018.

(51) Int. Cl.
| | | |
|---|---|---|
| *B23K 26/08* | (2014.01) | |
| *B23K 26/364* | (2014.01) | |
| *B23K 26/402* | (2014.01) | |
| *B29C 67/00* | (2017.01) | |
| *B23K 103/00* | (2006.01) | |

(52) U.S. Cl.
CPC ... *B23K 26/402* (2013.01); *A61M 2005/3101* (2013.01); *A61M 2205/0238* (2013.01); *A61M 2207/00* (2013.01); *B23K 2103/42* (2018.08)

(56) References Cited

U.S. PATENT DOCUMENTS

| | | |
|---|---|---|
| 2017/0173266 A1 | 6/2017 | Ashmead et al. |
| 2017/0281873 A1 | 10/2017 | Kaneko |
| 2018/0289897 A1 | 10/2018 | Kaneko et al. |

FOREIGN PATENT DOCUMENTS

| | | |
|---|---|---|
| JP | 2002-144376 A | 5/2002 |
| JP | 2005-118238 A | 5/2005 |
| JP | 2017-176540 A | 10/2017 |
| WO | 2012/166515 A1 | 12/2012 |
| WO | 2015/054282 A2 | 4/2015 |
| WO | WO2015118958 | 8/2015 |

SYRINGE AND GASKET SYSTEMS

CROSS-REFERENCE TO RELATED APPLICATIONS

This application is a United States National Phase Application filed under 35 U.S.C. § 371 from International Patent Application No. PCT/US2019/065099, filed Dec. 6, 2019, which claims benefit from U.S. Provisional Patent Application No. 62/776,958, filed Dec. 7, 2018; U.S. Provisional Application No. 62/788,168, filed Jan. 4, 2019; U.S. Provisional Application No. 62/789,366, filed Jan. 7, 2019; and U.S. Provisional Application No. 62/825,166, filed Mar. 28, 2019. The contents and disclosures of each of those applications are incorporated by reference herein in their entireties.

This application also incorporates by reference U.S. Pat. No. 7,985,188 B2, issued Jul. 26, 2011 and more particularly incorporates its disclosure of a syringe barrel or the like, lubricated by applying a PECVD coating of $SiO_xC_y$ or $SiO_xC_yH_z$, and for methods of making, testing and using such syringe barrels.

FIELD

The present disclosure relates to a matched syringe and plunger system, in particular a gasket to be used within the syringe, and an improved process of making and inspecting laser cuts in the gasket.

BACKGROUND OF THE DISCLOSURE

Prefilled parenteral containers, such as syringes or cartridges, and plunger systems have been developed to facilitate quick and accurate dosing of a sterile product (for example, a saline solution, a dye for injection, a pharmaceutically active preparation, etc), minimizing dosing errors, reducing the risk of biological contamination, enhancing the convenience and ease of use, preventing overfill of the product, etc (Yoshino et al. J Pharm Sci. 2014; 103(5):1520-8). Prefilled parenteral containers are typically sealed with a rubber gasket that is secured at the distal end to a plunger, which provides closure integrity over the shelf life of the container's contents. To use the prefilled syringe, the packaging and cap are removed, optionally a hypodermic needle or another delivery conduit is attached to the distal end of the barrel, the delivery conduit or syringe is moved to a use position (such as by inserting it into a subject's tissue or into apparatus to be rinsed with the contents of the syringe), and the plunger is advanced in the barrel to inject contents of the barrel to the point of application.

Seals provided by rubber gaskets in the barrel of the syringe typically involve the rubber of the gasket being pressed against the barrel. Typically, the maximum diameter of the rubber gasket is larger in diameter than the smallest internal diameter of the barrel. Thus, to displace the rubber gasket and its attached plunger when the injection product is to be dispensed from the syringe requires overcoming this pressing force of the rubber gasket. Moreover, not only does this pressing force provided by the rubber seal typically need to be overcome when initially moving the gasket secured to the plunger, but this force also needs to continue to be overcome as the rubber gasket is displaced along the barrel during the dispensing of the injection product. The need for relatively elevated forces to advance the gasket and plunger in the syringe may increase the user's difficulty in administering the injection product from the syringe. This is particularly problematic for auto injection systems where the syringe is placed into the auto injection device and the gasket is advanced by a fixed spring. Accordingly, primary considerations concerning the use of a gasket secured to a plunger in a prefilled parenteral container include: (1) container closure integrity ("CCI", defined below) and liquid/gas-tightness; and (2) plunger force (defined below) required to dispense syringe contents.

In practice, maintaining CCI/liquid or gas-tightness and providing desirable plunger force tend to be competing considerations. In other words, absent other factors, the tighter the fit between the gasket and the interior surface of the container to maintain adequate CCI/liquid or gas-tightness, the greater the force necessary to advance the gasket in use. In the field of syringes, it is important to ensure that the gasket secured to the plunger can move at a substantially constant speed and with a substantially constant and relatively low force when advanced in the barrel. In addition, the force necessary to initiate plunger movement and then continue advancement of the plunger should be low enough to enable comfortable administration by a user and prevent jolting or unnecessarily high pressing force that can cause patient discomfort.

To reduce friction and thus improve plunger force, lubrication is traditionally applied to the barrel-contacting engagement surface of the gasket secured to the plunger, the interior surface of the barrel, or both. Liquid or gel-like flowable lubricants, such as free silicone oil (e.g., polydimethylsiloxane or "PDMS"), may provide a desired level of lubrication between the plunger and the barrel to optimize plunger force. PDMS is, in fact, a standard flowable lubricant used in the industry. However, use of flowable lubricant between the gasket and the barrel is not desired. One reason is that a flowable lubricant can mix and interact with the drug product in a syringe, potentially degrading the drug or otherwise affecting its efficacy and/or safety. For example, silicone oil, when used as a lubricant, can cause droplets which could potentially result in aggregation of sensitive biopharmaceuticals or clouding of the solution (Bee J S et al. PDA J Pharm Sci Technol. 2014; 68(5):494-503), or cause drug interactions and increased particulate formation (Yamashita A et al. Adv Drug Deliv Rev. 2013; 65(1):139-47). Monoclonal antibodies, conjugate vaccines, and protein formulations are particularly vulnerable to silicone-induced protein aggregation and particle formation. (Majumdar et al. J Pharm Sci. 2011 July; 100(7):2563-73). In addition, over time, silicone migration can impact consistency of delivery, as it may change break loose and glide force (BLGF) and injection time (Thornton J D et al., 2015. ONdrugDelivery Magazine, Issue 61 (October 2015), pp 10-15). Subvisible particles caused by the migration of silicone oil into the drug formulation can introduce several product quality concerns, such as exceedance of USP limits for particulates in parenteral containers, structural instabilities in proteins caused by adsorption, and/or immunogenic responses caused by injection of silicone oil induced protein aggregates or silicone oil/protein complexes, which can reduce drug efficacy and/or cause potentially dangerous reactions in the patient, making the product unfit for use (Thornton J D et al., 2015. ONdrugDelivery Magazine, Issue 61 (October 2015), pp 10-15). Thus, lubricants may be problematic if they are injected into the patient along with the drug product.

In addition, flowable lubricants, when used with prefilled syringes, may migrate away from the gasket over time, resulting in spots between the gasket and the interior surface of the container with little or no lubrication. This may cause a phenomenon known as "sticktion," an industry term for the adhesion between the gasket and the barrel that needs to be overcome to break out the plunger and gasket and allow it to begin moving. For these reasons, there is an industry need for an "oil free" solution, i.e., a gasket that is free of flowable lubricant between the gasket and the barrel and wherein such flowable lubricant is absent from the drug product stream.

As an alternative (or in addition) to flowable lubricants, gaskets have been developed from materials having lubricious properties or to include friction-reduced coatings or films on their exterior surface. Such fluoropolymer films, in some embodiments, laminates, can provide a barrier to minimize the interaction between the formulation and the plunger while maintaining the gasket's seal integrity (Christa Jansen-Otten 2019. Blog; Westpharma). For example: the i-COATING by TERUMO, which is referred to in Canadian Patent No. 1,324,545, incorporated by reference herein in its entirety; W. L. Gore expanded PTFE film on a rubber stopper disclosed in EP2493534B1, incorporated by reference herein in its entirety; and the CZ plunger by WEST. However, such gaskets have experienced failures in CCI due to film wrinkling, defects in the film and/or film delamination from the rubber gasket may also have inferior gas-barrier properties. Accordingly, a conventional fluoropolymer film laminated gasket alone may not be a viable solution for a prefilled syringe that houses product which is sensitive to certain gases. Moreover, such a syringe and gasket system has inferior CCI.

Further, in such prefilled syringe systems, the gasket is in contact with the enclosed sterile product during administration and the drug storage period. Interactions between the sterile product and its packaging can have a significant impact on the purity and degradation of the formulation and the safety of patients administered that product (Christa Jansen-Otten 2019. Blog; Westpharma). The selection of the right gasket for a syringe system, in particular, a prefilled syringe system is therefore an important consideration for the pharmaceutical and biopharmaceutical industry.

U.S. patent application Ser. No. 15/445,108, incorporated by reference herein in its entirety, discloses a laminated gasket for use in a medical syringe. Such a gasket includes a main body made of an elastic material, and a film provided on a surface of the main body. In a syringe system, a syringe typically includes a syringe barrel and a plunger reciprocally movable in the syringe barrel. The gasket is attached to the distal end of the plunger. In this application, the gasket is further subjected to a laser processing process by applying a laser beam to the circumferential surface portion of the gasket obliquely with respect to the circumferential surface portion, while rotating the circumferential surface portion of the gasket about a center axis of the gasket, thereby forming an annular groove circumferentially in at least a surface portion of the film on the gasket. Such a laser-cut groove or channel improves the slidability and sealability of the laminated gasket within a syringe, while maintaining the elasticity of the gasket, and minimizing liquid leakage from a prefilled syringe.

In the process disclosed in U.S. patent application Ser. No. 15/445,108, the internal cavity of the gasket contains threads to attach a threaded plunger rod, which is then rotated during the laser cut process. However, this method of securing the gasket during the laser process has several disadvantages because the walls of the gasket may deform or sag while the gasket is being rotated to create the laser-cut groove. This results in a less consistent laser cut or groove on the gasket film. A syringe system incorporating a gasket produced by the process of U.S. patent application Ser. No. 15/445,108 is also more prone to liquid or gas leakage and has an inferior CCI.

SUMMARY OF THE DISCLOSURE

Thus, there is a need for an improved process for producing one or more channels on the surface of a gasket, on whose outer surface resides a film, as well as improved gaskets for use in syringe-gasket systems for the delivery of, for example, drug products to subjects in need thereof. The resulting gasket has improved prevention of liquid or gas leakage, and has superior CCI when used in a matched syringe and plunger system. A syringe assembled with an improved gasket of the present disclosure improves the protection of the product contained within it, and is characterized by improved product shelf life.

The present application provides an improved process for making one or more continuous channels in a film residing on the outer surface of a gasket, in some embodiments extending into the gasket itself, for use in matched syringe and plunger-gasket systems which results in superior container closure integrity and sealability and minimal liquid/gas leakage.

In some embodiments, the disclosure of this application provides gaskets with improved channels for use in matched syringe-plunger systems. The silicone oil-free syringe and gasket systems of some embodiments of this disclosure, preferably prefilled plastic syringe systems, have superior container closure integrity (CCI), avoid high break loose forces and liquid/gas leakage, produce consistent delivery performance over time, provide protection of the enclosed product, minimize interaction with the product, and maintain efficacy and sterility during the shelf life of the product, and have improved shelf life. The syringe and gasket systems of some embodiments also produce reduced sub-visible particles and can protect complex or sensitive biologics contained within the syringe from silicone oil-induced aggregation and particulation. The disclosure in some embodiments also provides an improved process for making continuous channels in the gasket and film residing on its outer surface by laser cuts.

In some embodiments, the disclosure also provides an improved process for producing silicone oil free syringe and gasket systems that has fewer than 300 particles of 2 micron size or more, measured using light obscuration (LO) or microflow imaging (MFI). Further, in some embodiments, the syringe system of the present disclosure incorporates a process of improving the sealability provided by the built-in lubrication film on a gasket that eliminates the need to use a lubricated syringe barrel. In other embodiments, the present disclosure incorporates state of the art manufacturing process control and 100% inspection systems which provide tight dimensional control of the gasket and corresponding syringe and channels, thereby enabling a highly consistent compression of the assembled syringe and gasket system to be optimized for container closure integrity and plunger forces.

Particular embodiments of the disclosure are set forth in the following numbered paragraphs:

1. A process for making one or more continuous channels in a film residing on at least a circumferential outer surface portion of a gasket, the gasket comprising a main body made of an elastic material, the main body having a circumferential surface portion and an internal cavity in its center, the cavity being defined by an inner surface portion of the gasket and being open at one end, the process comprising the following steps:
  (a) inserting a portion of one end of a mandrel into the open end of the cavity;
  (b) securing the gasket to the mandrel;
  (c) positioning the mandrel and secured gasket in proximity to a laser; and
  (d) applying a laser beam emitted from the laser to one or more selected locations on a surface portion of the film residing on the circumferential outer surface portion of the gasket while rotating the mandrel and the secured gasket along the mandrel's longitudinal axis to produce one or more continuous channels in the film, the channels extending around the entire circumference of a circumferential outer surface of the gasket.

2. The process of paragraph 1, wherein the thickness of the film on the surface of the gasket prior to step (d) is about 10-30 microns, about 15-35 microns, about 20-50 microns, or about 20 microns.

3. The process of paragraph 1 or 2, wherein the film has one or more of good slidability and chemical stability.

4. The process of any one of paragraphs 1-2, wherein the film is capable of preventing migration of components from the elastic material of the gasket.

5. The process of any one of paragraphs 1-4, wherein the gasket is secured to the mandrel by press-fit assembly.

6. The process of paragraph 5, wherein the diameter of at least a part of the mandrel portion that is inserted into the internal cavity of the gasket is greater than the inner diameter of the cavity.

7. The process of any one of paragraphs 1-6, wherein when more than one channel is produced, the channels are axially spaced.

8. The process of any one of paragraphs 1-7, wherein the one or more channels have axially opposed first and second side walls and a floor.

9. The process of any one of paragraphs 1-8, wherein the one or more channels each independently have an axial width between the side walls selected from 1-100 microns, 5-50 microns, 10-30 microns, and 15-25 microns.

10. The process of any one of paragraphs 1-9, wherein the one or more channels each independently have a radial depth selected from 0-100 microns, 5-50 microns, 10-30 microns, and 15-25 microns.

11. The process of any one of paragraphs 1-10, wherein the one or more channels each independently have a laser-cut depth selected from 20-80 microns, 30-60 microns, 40-50 microns, 50-60 microns, 40-45 microns, 45-50 microns, 50-55 microns and 55-60 microns.

12. The process of any one of paragraphs 1-11, wherein the one or more channels extend through the film into the outer surface portion of the gasket.

13. The process of any one of paragraphs 1-12, wherein the one or more channels comprise a first circumferentially extending lip located adjacent to the first side wall of the channel and extending radially above the film.

14. The process of paragraph 13, wherein the one or more channels further comprise a second circumferentially extending lip located adjacent to the second side wall and extending radially above the film.

15. The process of paragraph 13 or 14, wherein the first and second lips independently have a peak height selected from 10-100 microns, 15-60 microns, 20-50 microns, or 30-40 microns.

16. The process of any one of paragraphs 13-15, wherein the first and second lips of each of the one or more channels independently have a peak width selected from 200-1,000 micron, 275-550 microns, 300-400 microns, or 450-500 microns.

17. The process of any one of paragraphs 13-16, wherein each lip comprises film material.

18. The process of any one of paragraphs 13-16, wherein each lip comprises film material displaced from the channel by the laser beam as the channel is produced.

19. The process of any one of paragraphs 13-18, wherein at least one lip is capable of being positioned in a tubular syringe barrel so as to form a seal against the inner surface of the barrel.

20. The process of any one of any one of paragraphs 1-19, wherein the position of the laser relative to the mandrel and secured gasket is controlled by a servo-motor.

21. The process of any one of paragraphs 1-20, wherein the film is a fluoropolymer film.

22. The process of paragraph 21, wherein the fluoropolymer film is polytetrafluoroethylene (PTFE).

23. The process of any one of paragraphs 1-22, wherein the elastic material comprises bromobutyl rubber.

24. The process of any one of paragraphs 1-23, wherein an inner surface of the film is treated prior to being applied to an outer surface portion of the gasket to promote adhesion to said outer surface portion.

25. The process of paragraph 24, wherein the inner surface of the film is corona treated.

26. The process of paragraph 24, wherein the inner surface of the film is chemically treated.

27. The process of any one of paragraphs 1-26, wherein the dimensional tolerance of gaskets capable of being used in the process is selected from ±100 micron, ±50 microns, ±35 microns, ±25 microns, ±20 microns, ±15 microns, ±10 microns, ±5 microns, or ±3 microns.

28. The process of any one of paragraphs 1-27, wherein the gasket has fewer than 300 particles of 2 micron size or more, measured using light obscuration (LO) or microflow imaging (MFI).

29. A matched syringe and plunger system comprising:
  (a) a tubular syringe barrel;
  (b) a plunger located inside the syringe barrel and being reciprocally movable longitudinally in the barrel; and
  (c) a gasket attached to the distal end of the plunger; the gasket comprising a main body made of an elastic material, the main body having a circumferential outer surface portion and an internal cavity in its center, the cavity being defined by an inner surface portion of the gasket and being open at one end, wherein the gasket is characterized by one or more continuous channels made according to a process comprising the following steps:
  (i) inserting a portion of one end of a mandrel into the open end of the cavity;
  (ii) securing the gasket to the mandrel;
  (iii) positioning the mandrel and secured gasket in proximity to a laser; and
  (iv) applying a laser beam emitted from the laser to one or more selected locations on a surface portion of the film residing on the circumferential outer surface portion of the gasket while rotating the mandrel and the secured gasket along the mandrel's longitudinal axis to produce one or more continuous channels in the film, the channels extending around the entire circumference of a circumferential outer surface of the gasket.

30. The system of paragraph 29, wherein the gasket is attached to the plunger by press-fit assembly.

31. The system of paragraph 30, wherein the syringe barrel contains an injectable fluid distal of the gasket.

32. The system of any one of paragraphs 29-31, having a container closure integrity (CCI) with a defect rate of no more than 6-sigma.

33. The system of any one of paragraphs 29-32, wherein the plunger and attached gasket has a break loose force between 4 and 20 Newtons (N).

34. The system of any one of paragraphs 29-33, wherein the plunger and attached gasket has a glide force between 4 and 20 Newtons (N).

35. The system of paragraph 33 or 34, wherein the break loose force or glide force changes less than about 10-30% over a two-year storage life.

36. The system of any one of paragraphs 29-35, wherein the syringe barrel comprises a wall having an inner surface coated with a lubricity layer having the atomic ratios 1 atom of Si: 0.5 to 2.4 atoms of O: 0.6 to 3 atoms of C measured by x-ray photoelectron spectroscopy (XPS).

37. The system of paragraph 36, wherein the syringe barrel further comprises a trilayer coating between the inner surface of the wall and the lubricity coating, wherein the trilayer comprises a tie coating, a barrier coating, and a pH protective coating; wherein
  (a) the tie coating comprising $SiO_xC_y$ or $SiN_xC_y$, wherein x is from about 0.5 to about 2.4 and y is from about 0.6 to about 3, the tie coating having an outer surface facing the inner surface of the wall and the tie coating having an interior surface facing the lumen of the syringe barrel;
  (b) the barrier coating comprising $SiO_x$, wherein x is from 1.5 to 2.9, the barrier coating being from 2 to 1000 nm thick, the barrier coating having an outer surface facing the interior surface of the tie coating and the barrier coating having an interior surface facing the lumen of the syringe barrel; and
  (c) the pH protective coating comprising $SiO_xC_y$ or $SiN_xC_y$, wherein x is from about 0.5 to about 2.4 and y is from about 0.6 to about 3, the pH protective coating having an outer surface facing the interior surface of the barrier coating and an interior surface facing the lumen of the syringe barrel.

38. The system of paragraph 36 or 37, wherein the lubricity layer is capable of reducing one or both of the sticktion and sliding friction of the gasket in the barrel, compared to one or both of the sticktion and sliding friction of the gasket in the barrel absent the lubricity layer.

39. The system of any one of paragraphs 29-38, wherein the film is a fluoropolymer film.

40. The system of any one of paragraphs 29-39, wherein the fluoropolymer film is polytetrafluoroethylene (PTFE).

41. The system of any one of paragraphs 29-40, wherein the one or more of said channels improve the container closure integrity of the syringe components when assembled to form a prefilled syringe, compared to an otherwise substantially similar prefilled syringe which does not include a channel produced by said process.

42. The system of paragraph 41, wherein the improvement is a longer shelf life.

43. The system of paragraph 41 or 42, wherein the improvement is measured by vacuum decay leak detection method.

44. The system of paragraph 41 or 42, wherein the improvement is measured by a liquid CCI test method.

45. The matched syringe and plunger system of any one of paragraphs 29-44, wherein the syringe barrel has a wall including an inner surface defining a generally cylindrical lumen, the barrel having an inner diameter;
the gasket having a leading face, a side surface, a trailing portion, and an outer diameter;
the gasket configured to be received within any the barrel with the gasket outer diameter located within and movable with respect to the barrel inner diameter; and
the barrel and gasket of the system respectively sized to provide spacing between the smallest barrel inner diameter and largest gasket outer diameter, when assembled, deviating from the nominal spacing by no more than: ±100 microns, ±50 microns, ±35 microns, ±25 microns, ±20 microns, ±15 microns, ±10 microns, ±5 microns or ±2 microns.

46. A gasket comprising
(a) a main body made of an elastic material, the main body having a circumferential surface portion and an internal cavity, the cavity being defined by an inner surface portion of the gasket and being open ended at one end;
(b) a film residing on at least a circumferential outer portion of the gasket; and
(c) one or more continuous channels in the film, the channels extending around the entire circumferential outer surface of the subject;
wherein the gasket has one or more of the following characteristics:
  (i) a container closure integrity (CCI) when assembled within a matched syringe and plunger system with a defect rate of no more than 6-sigma;
  (ii) a break loose force between 4 and 20 Newtons (N) when assembled within a matched syringe and plunger system;
  (iii) a glide force between 4 and 20 Newtons (N) when assembled within a matched syringe and plunger system;
wherein the break loose force or glide force changes less than about 10-30% over a two-year storage life.

Figure 1:
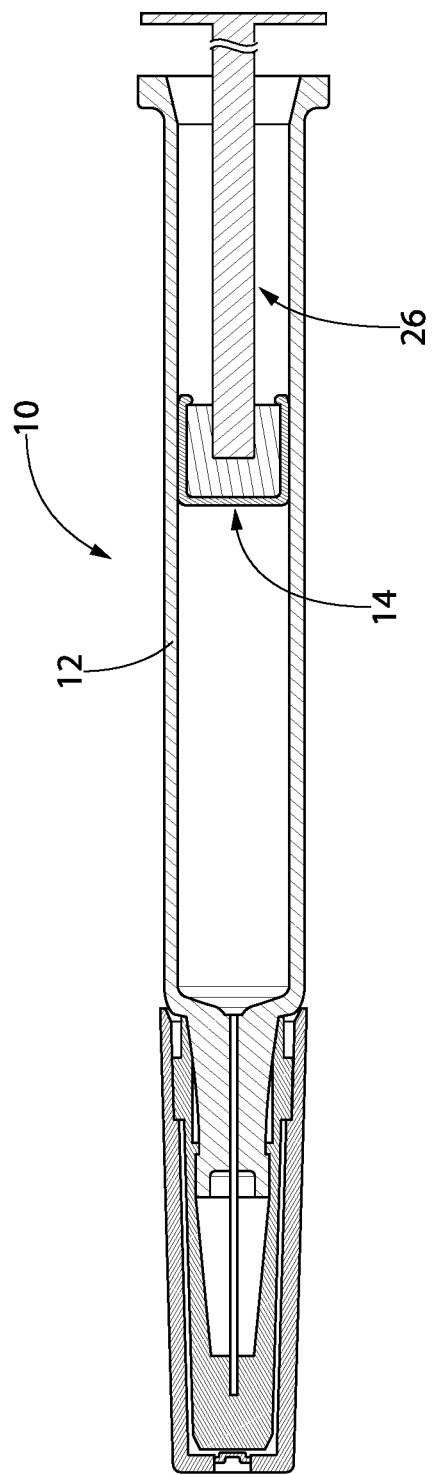
FIG. 1 shows a sectional view of a syringe 10 comprising a syringe barrel 12 assembled with a gasket 14 attached to a plunger 26.

The following reference characters are used in the drawing figures according to any embodiment:

| | |
|---|---|
| 10 | Syringe |
| 12 | Syringe barrel |
| 14 | Gasket |
| 16 | Film |
| 18 | Gasket core |
| 20 | Channel |
| 22 | First lip of channel |
| 24 | Second lip of channel |
| 26 | Plunger |
| 28 | Mandrel |

Definitions

In the context of the present disclosure, the following definitions and abbreviations are used:

The word "comprising" according to any embodiment does not exclude other elements or steps, and the indefinite article "a" or "an" does not exclude a plurality unless indicated otherwise. Whenever a parameter range is indicated, it is intended to disclose the parameter values given as limits of the range and all values of the parameter falling within said range. Reference to "about" a value or parameter herein includes (and describes) embodiments that are directed to that value or parameter per se. For example, description referring to "about X" includes description of "X." Numeric ranges are inclusive of the numbers defining the range. As used herein, the term "about" permits a variation of ±10% within the range of the significant digit.

Where aspects or embodiments are described in terms of a Markush group or other grouping of alternatives, the present application encompasses not only the entire group listed as a whole, but each member of the group individually and all possible subgroups of the main group, and also the main group absent one or more of the group members. The present application also envisages the explicit exclusion of one or more of any of the group members in the embodimented disclosure.

Exemplary methods and materials are described herein, although methods and materials similar or equivalent to those described herein can also be used in the practice or testing of the various aspects and embodiments. The materials, methods, and examples are illustrative only and not intended to be limiting.

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

As used herein, the term "syringe" is broadly defined to include cartridges, injection pens, and other types of barrels or reservoirs adapted to be assembled with one or more other components to provide a functional syringe. "Syringe" is also broadly defined to include related articles such as auto-injectors, which provide a mechanism for dispensing the contents. Preferably, "syringe" may include prefilled syringes. A "syringe" as used herein may also apply to vaccine dispensing syringes comprising a product space containing a vaccine. A "syringe" as used herein may also have applications in diagnostics, e.g., a sampling device comprising a medical barrel prefilled with a diagnostic agent (e.g., contrast dye) or the like. Broadly, a "syringe" as used herein is any medical barrel, which when assembled with one or more other components (e.g. a gasket and a plunger), functions as a container/dispenser of flowable product. Though the disclosure is not necessarily limited to syringes of a particular volume, syringes are contemplated in which the lumen has a void volume of, for example, from 0.5 to 50 mL, optionally from 1 to 10 mL, optionally from 0.5 to 5 mL, optionally from 1 to 3 mL. A syringe of the present disclosure includes a hollow cylindrical syringe barrel 12, a plunger 26 combined with the syringe barrel and reciprocally movable in the syringe barrel 12, and a gasket 14 attached to a distal end of the plunger 26. See FIG. 1.

Figure 2:
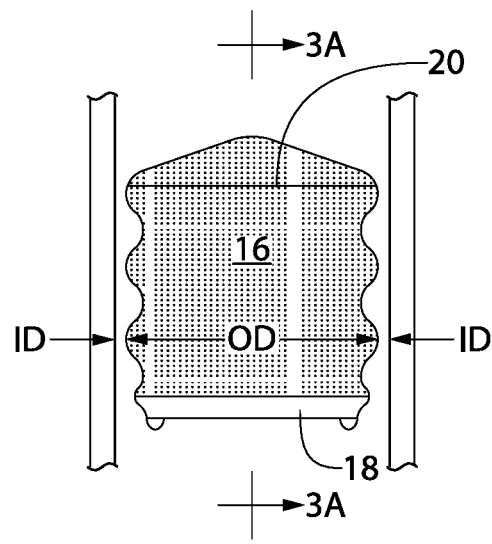
FIG. 2 shows a fragmentary detail view of the syringe of FIG. 1, showing the inner diameter (ID) of the barrel 12 and the outer diameter (OD) of the gasket 14 that are matched to be within the predetermined tolerance between them, and also showing a film 16 on the outer surface of a gasket core 18 and a continuous channel 20 in the film residing on a circumferential outer surface portion of the gasket core 18, the channel 20 encircling the gasket 14. The channel has lips 22 and 24 as shown in FIG. 3B.
Figure 3A:
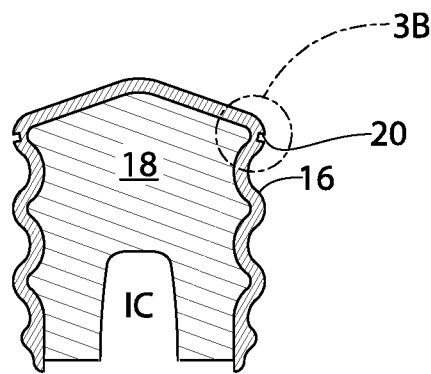
FIG. 3A shows a schematic sectional view taken along section lines 3A-3A of FIG. 2, showing the gasket core 18 with in internal cavity (IC), film 16, and channel 20 in the surface of the film (in some embodiments channel 20 extends through the film into the outer surface of the gasket (not shown)) and encircling a circumferential outer surface portion of the gasket 14.

As used herein, the term "gasket" in the context of the present disclosure is a shaped piece or ring made of an elastomeric material that can be used to mechanically seal the space between two opposing inner surfaces of a syringe barrel. A gasket is preferably cylindrical in shape with a short axis. The gasket has a circumferential surface portion to be kept in substantially gas-tight and liquid-tight contact with an inner peripheral surface of the syringe barrel. A gasket of the present disclosure is a gasket comprising a main body made of an elastic material and a film residing on at least a circumferential surface of the main body, the gasket having a circumferential surface portion and an internal cavity (IC) in its center, the cavity being defined by the inner surface of the gasket and being open at one end. See FIG. 2 and FIG. 3A. In preferred embodiments, the internal cavity of the gasket is not threaded.

The "elastic material" may be rubber or an elastomer. Particularly, preferred types of rubber are include butyl rubbers, chlorinated butyl rubbers and brominated butyl rubbers. Other types of elastic material may include thermosetting rubbers and dynamically crosslinkable thermoplastic elastomers having crosslinking sites are which make them heat-resistant. These polymer components of such elastomers include ethylene-propylene-diene rubbers and butadiene rubbers.

As used herein, the term "film" is a material residing on at least a circumferential outer surface portion of the main body of the gasket. Preferably, it coats or resides on substantially all of the outer surfaces of the gasket. The film may have an optional thickness of under about 100 micrometer (μm or microns), optionally from about 10-30 microns, about 15-35 microns, or about 20-50 microns. Most preferably, the film is about 20 microns in thickness. A variety of different materials may be employed for the film, such as, for example, an inert fluoropolymer, including, fluorinated ethylene propylene (FEP), ethylene tetrafluoroethylene (ETFE), polytetrafluoroethylene (PTFE), ethylene perfluoroethylenepropylene (EFEP), ethylene chlorotrifluoroethylene (ECTFE), Polychlorotrifluoroethene (PCTFE), perfluoroalkoxy (PFA), among other coatings. Preferably, the film is an ultrahigh molecular weight polyethylene film (UHMWPE) or a fluoropolymer film. Fluoropolymer films such as polytetrafluoroethylene (PTFE) are preferred because of their excellent slidability and chemical stability. The type of the film to be provided on the surface of the main body of the gasket is not particularly limited, as long as the film is capable of preventing migration of substances from the crosslinked rubber (main body) and has a slidability, i.e., a smaller friction coefficient, as compared to the main body of the gasket.

Optionally, the film may comprise CPT fluoropolymer. CPT is a modified perfluoroalkoxy (PFA) that generally comprises the addition of PCTFE side chains to a PFA main chain during polymerization.

Optionally, additives may also be added to the film material for the film, such as additives that may improve the adhesion of the film to the underlying portion of the gasket to make a liquid sealing section and/or decrease the friction between that section and the sidewall of the syringe barrel. Additionally, according to certain embodiments, an adhesion promoting coating or process may be employed, such as, for example, a corona treatment or a chemical treatment. Corona treatment or air plasma is a surface modification technique that uses a low temperature corona discharge plasma to impart changes in the properties of a surface. The corona plasma is generated by the application of high voltage to an electrode that has a sharp tip. For some applications, it may be desirable to coextrude different materials to form the film. For example, coextruded film combinations may include a cyclic olefin copolymer (COC) with Aclar, Polyethylene (PE) with Aclar and FEP with PE, among other combinations.

As used herein, the term "mandrel" refers to a device or tool which may be attached at its distal end to a base that keeps the body of the mandrel steady and secured but one that allows the mandrel to rotate along its longitudinal axis. The proximal portion of the mandrel has a shape similar to the male portion of a two-part mold, which can be inserted and secured within the internal cavity (the corresponding female portion) of a gasket. In some embodiments, the mandrel is a shaped bar of metal or steel, such as a cylindrical rod. The proximal end of the mandrel may be continuous with the body of the mandrel or may have a smaller or larger circumferential portion than distal sections of the mandrel. In preferred embodiments, the proximal end of the mandrel is secured to the gasket using "press-fit assembly" in which is the gasket is secured to the mandrel by friction after the parts are pushed together, rather than by any other means of fastening (such as screwing). In some embodiments, the diameter of at least a part of the mandrel portion that is inserted into the internal cavity of the gasket is greater than the inner diameter of the cavity. "Securing the gasket" to the mandrel refers to ensuring that the gasket is fixed or fastened to the proximal end of the mandrel so as to not give way, become loose, or move independently of the mandrel. A gasket secured onto the mandrel will maintain the shape of its inner and outer walls and will not collapse or deform during the laser cut process. "Positioning" the mandrel and secured gasket in proximity to a laser refers to fixing the base of the mandrel at a desired position in relation to the laser beam, such that the base of the mandrel will be in a rigid non-moving position during the laser beam process of the present disclosure. However, the mandrel will still be capable of rotating along its longitudinal axis. See FIG. 4A.

Figure 3B:
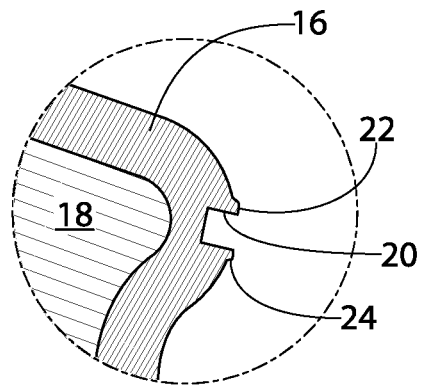
FIG. 3B shows a fragmentary detail view of the structure of FIG. 3A, showing one embodiment of a channel 20 and lips 22 and 24 on the respective sides of the channel 20.
Figure 5A:
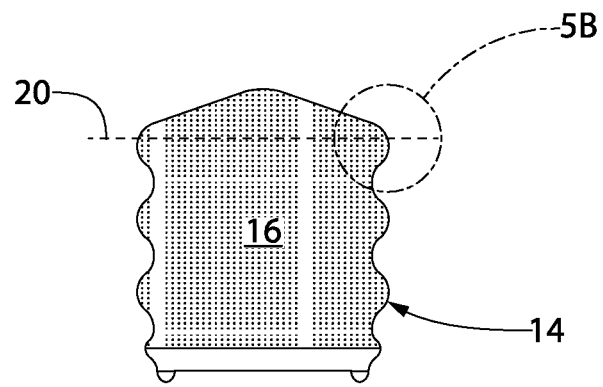
FIG. 5A is shows a gasket 14 with a film 16 with channel 20 in the film 16.
Figure 5B:
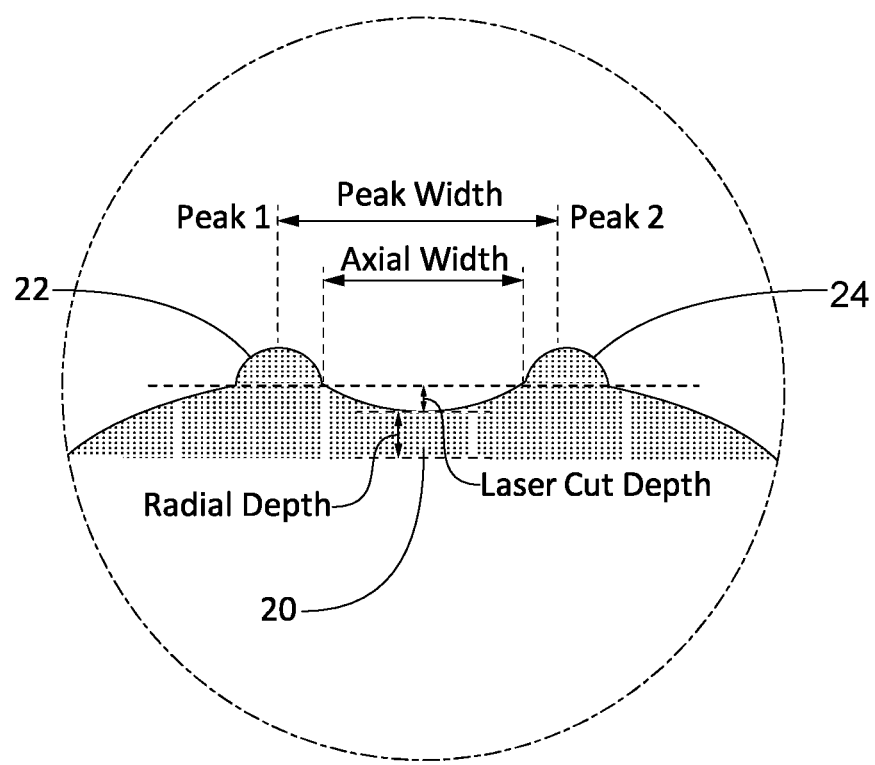
FIG. 5B shows a fragmentary detail view of the structure of FIG. 5A, showing an embodiment of a channel 20 in the surface of the film with lips 22 and 24 on the respective sides of the channel 20 and the various dimensions of the channel 20 and lips 22 and 24 (peak width, axial width, laser cut depth and radial depth). In other, more preferred embodiments, channel 20 extends into the outer surface of the gasket (not shown).

As used herein, the term "channel" refers to a cut in the film residing on the surface of the gasket by the laser cut. The term channel may be used interchangeably with the term "cut". In the present disclosure, the term "cut" may also refer to the process of using one or more laser beams to create a nick or separation of the film residing on at least a circumferential outer surface portion of a gasket. In some embodiments, the channel is cut in the surface portion of the film. In more preferred embodiments, the channel extends through the film into the outer surface of the gasket. One or more such channels can be produced, each encircling the gasket. When more than one channel is present, they are preferably axially spaced from one another. Each channel has two lips. The term "lip" refers to the structure created due to the pile-up of film material along either side of the channel that is created by the laser beam cut. The channel lips 22 and 24 are shown in FIG. 3B and FIG. 5B. Each lip is a raised rib positioned to seal against the barrel inner surface. Thus, each channel has two lips comprising two sealing ribs or peaks. In the present disclosure, the terms "lip", "rib" "peak" and "micro projections" are interchangeable.

The laser cut and the resulting channels are characterized by various dimensions, including, laser cut depth, radial depth, peak width, axial width, and peak height. The "laser cut depth" is measured from the surface of the uncut gasket film down to the lowest point in the trough of the channel. See FIG. 5B. The laser cut depth for the one or more channels is independently selected from the following ranges: 20-80 microns, 30-60 microns, 40-50 microns, 50-60 microns, 40-45 microns, 45-50 microns, 50-55 microns and 55-60 microns. The "radial depth" is measured from the uncut outer surface of the gasket up to the lowest trough in the channel. See FIG. 5B. The radial depth for the one or more channels that may be independently selected from the following ranges: 0 to 100 microns, 5 to 50 microns, 10 to 30 microns, and 15 to 25 microns. The "peak width" is the distance between two peaks of two lips on either side of a channel. Peak width is measured from the top of the peaks. See FIG. 5B. The peak width may be one of the following ranges: 200-1,000 micron, 275-550 microns, 300-400 microns, and 450-500 microns.

The circumferential continuous channel of the present disclosure has axially opposed "first and second side walls" and a "floor". The floor of the channel may be either a film surface or more preferably a gasket surface, depending on the thickness of the film and the depth of the cut. The "axial width" is measured from the first side wall to the second side wall of the channel across the breadth of the channel floor. In other words, the "axial width" is measured from one end of a channel to the other end of the channel across its breadth at the baseline level, i.e., at the laser uncut outer surface level of the film or gasket. The one or more channel independently has an axial width between the side walls of one of the following ranges: 1 to 100 microns, 5 to 50 microns, 10 to 30 microns, and 15 to 25 microns.

The "peak height" is measured from the surface of the uncut gasket film up to the highest peak of the lip created by the laser beam along the central axis of the peak, i.e., perpendicular to the surface of the film. The peak height of the lip on one or more of the channels is independently selected from one of the following ranges: 10-100 microns, 15-60 microns, 20-50 microns, and 30-40 microns.

As used herein, the term "Container closure integrity" or "CCI" refers to the ability of a container closure system, e.g., a plunger attached to a gasket disposed in a syringe barrel, preferably a prefilled syringe barrel, to provide protection and maintain efficacy and sterility during the shelf life of a sterile product contained in the container. In some embodiments, the container closure integrity is related to the sealability of a syringe system of the present disclosure. The one or more channels created by the laser in the film is intended to enhance the CCI of the plunger attached the gasket when assembled into a pre-filled syringe, by providing a physical break in the film that prevents defects in the film (such as delamination, tearing, or wrinkling) from adversely affecting the seal integrity between the gasket and the syringe. Container Closure Integrity (CCI) must be substantially maintained throughout the shelf life of a syringe of the present disclosure. CCI is an important characteristic of a pre-filled syringe for parenteral drug products contained within the syringe. One important element of CCI is maintaining a sterile barrier. The improved process of the present disclosure for producing one or more channels on a film reduces the likelihood of a CCI failure (breach of sterility), and/or facilitates a longer shelf life.

As used herein, the term "break loose force" refers to the force required to initiate movement of the plunger attached to a gasket in a syringe, for example in a prefilled syringe. It is the maximum force required to break the static friction of the gasket attached to a plunger. Break loose force is synonymous with "plunger force", "plunger breakout force", "breakout force", "initiation force" and "Fi" in the context of the present disclosure.

As used herein, the term "glide force" refers to the force required to maintain plunger movement (when the plunger is attached to a gasket of the present disclosure) in a syringe barrel once static friction has been overcome, e.g., during aspiration or dispense. Glide force is synonymous with "pushing force", "plunger sliding force", "maintenance force", and "Fm" in the context of the present disclosure.

As used herein, the terms "break loose force" "glide force", are collectively referred to as "BLGF forces", i.e., the various forces of the plunger and attached gasket of the present disclosure. The BLGF forces can be measured using any well-known test in the art, such as ISO 7886-1:1993. For example, the BLGF forces can be tested by filling a syringe of the disclosure with 1 ml of a liquid (such as water) and thereafter vacuum loading the stopper. The plunger force can be tested with a plastic threaded rod at 300 mm/min. In the present disclosure, the improved process of producing channels on the surface of gaskets prevents plunger force aging (i.e., an increase in break loose force over time). A matched syringe-plunger system of the present disclosure maintains a break loose force and a glide force of between 4 and 20 Newtons (N), that changes less than about 10%-30% over a two-year storage life. The process of the present disclosure provides consistent break loose and glide forces by incorporating manufacturing process control and 100% inspection systems.

As used herein, the term "sticktion" refers to a phenomenon that is an industry term for the adhesion between the plunger (attached to a gasket) and the syringe barrel that needs to be overcome to break out the plunger attached to the barrel and allow it to begin moving. The term "sliding friction" or "kinetic friction" refers to the resistance created by two objects sliding against each other. Sliding friction is intended to stop an object from moving. In the present disclosure, the lubricity layer within the syringe barrel is capable of reducing one or both of the sticktion and sliding friction of the gasket in the barrel, compared to one or both of the sticktion and sliding friction of the gasket in the barrel in the absence of the lubricity layer.

As used herein, the term "dimensional tolerance", "dimensional precision" or "dimensional consistency" is the degree of control over the dimensions of a part (Quality management for the Technology Sector (2000) 142-158). The dimensional tolerance is the permissible limit of variation of the physical dimensions of the various parts of the present disclosure, such as the gasket and the syringe barrel. The "tolerance" is the allowable variation for any given size of the gasket or syringe barrel of the present disclosure which permits proper functioning of the syringe system. In other words, the dimensional tolerance is the allowable variation to the dimensions of the syringe or gasket of the present disclosure that does not compromise one or more of the following properties: container closure integrity, BLGF forces, sealability, leakage properties, slidability, etc. The dimensional tolerance among gaskets capable of being used in the process of the present disclosure is selected from ±100 micron, ±50 microns, ±35 microns, ±25 microns, ±20 microns, ±15 microns, ±10 microns, ±5 microns, or ±3 microns. The term "nominal spacing" in the syringe system of the present disclosure is related to dimensional tolerance. In the barrel and gasket of the system of the disclosure, respectively sized to provide spacing between the smallest barrel inner diameter and largest gasket outer diameter, when assembled, deviates from the nominal spacing by no more than: ±100 microns, ±50 microns, ±35 microns, ±25 microns, ±20 microns, ±15 microns, ±10 microns, ±5 microns or ±2 microns.

DETAILED DESCRIPTION

The present disclosure in some embodiments will now be described more fully, with reference to the accompanying drawings. This disclosure can, however, be embodied in many different forms and should not be construed as limited to the embodiments set forth here. Rather, these embodiments are examples, which has the full scope indicated by the language of the claims. Like numbers refer to like or corresponding elements throughout.

Laser Process Embodiments

Figure 4A:
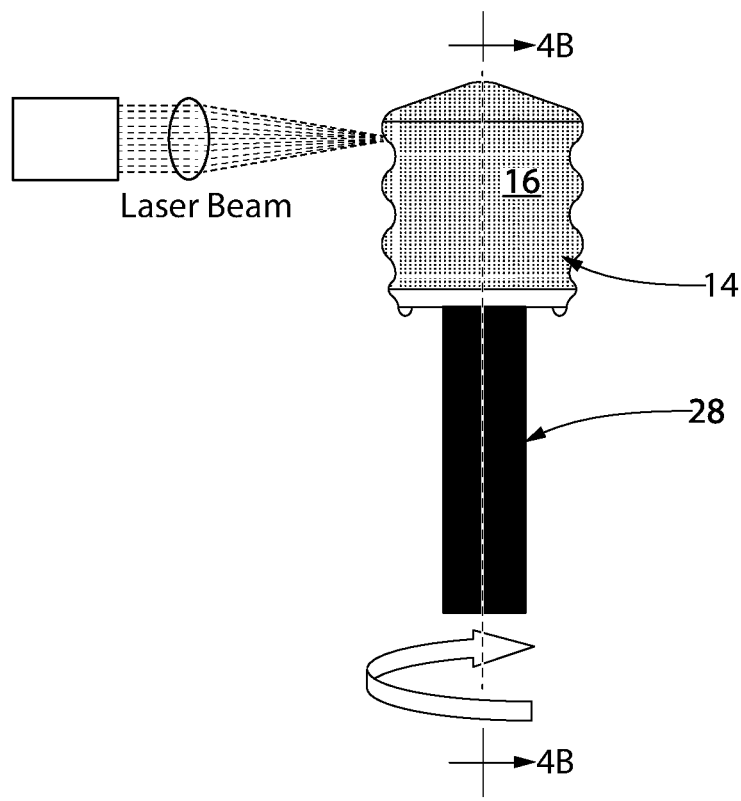
FIG. 4A shows an assembly of a gasket 14 and a mandrel 28 inserted into the internal cavity of the gasket. The figure also depicts applying a laser beam obliquely to an outer portion of a film 16 residing on a circumferential outer surface portion of the gasket 14 which is secured to the mandrel 28, while the mandrel 28 and gasket 14 are being rotated along the mandrel's longitudinal axis to produce a continuous channel 20 in the film 16 residing on a circumferential outer portion of the gasket 20.
Figure 4B:
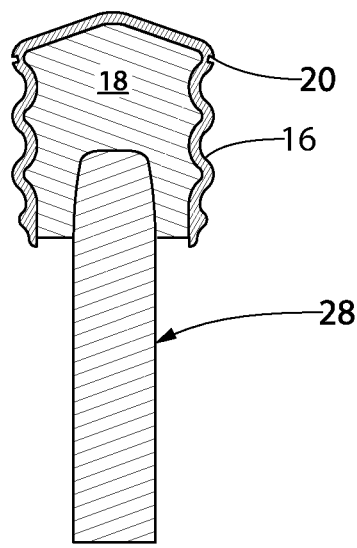
FIG. 4B shows a schematic sectional view of one embodiment of the gasket taken along section lines 4B-4B of FIG. 4A, showing the mandrel 28 secured in the gasket internal cavity, film 16, and a channel 20 in the outer surface of the film 16 residing on a circumferential outer surface portion of the gasket 20 and encircling it. In other embodiments the channel extends through the film and into the outer surface of the gasket.

FIG. 4A, is a diagram of the laser processing process of one embodiment of the disclosure. Referring to FIG. 4A, a laser beam is applied at a desired angle to the circumferential surface portion of a gasket 14 which is secured on a mandrel 28. For the formation of channels in the circumferential surface portion of the gasket, a laser beam source is fixed with respect to the circumferential surface portion of the gasket 14 with a film 16 residing on the outer surface of the gasket, and the laser beam is applied to the circumferential surface portion while the gasket 14 secured to the mandrel 28 is rotated about the longitudinal axis thereof. Thus, the laser beam can be applied at the predetermined incident angle α to any angular position of the circumferential surface portion, whereby the channel is formed uniformly.

While the laser beam is applied obliquely to the circumferential surface portion, the gasket is rotated in a rotation direction such that the circumferential surface portion is moved away from a laser beam application position at which the laser beam is applied (in FIG. 4A, the gasket is rotated clockwise).

By thus performing the laser processing process of this embodiment of the disclosure, the channel is substantially uniformly formed in the film and more preferably extending into the circumferential surface portion of the gasket and, at the same time, the outer edge portions 22 and 24 are formed (FIG. 5B).

Syringe and Plunger System Embodiments

In FIG. 1, one exemplary embodiment of a matched syringe and plunger system of this disclosure including a gasket 14 and a plunger 26 constructed in accordance with one aspect of this disclosure is shown. The terms "distal" and "proximal" refer generally to a spatial or positional relationship relative to a given reference point, wherein "proximal" is a location at or comparatively closer to that reference point and "distal" is a location further from that reference point. As applied herein to the plunger 26, for example, the relevant reference point is the bottom end of the plunger 26, the distal end, which is attached to the gasket 14. As applied herein to the syringe barrel 12, for example, the relevant reference point is the bottom end of the barrel 12, the distal end, which is attached to a delivery conduit or syringe.

The syringe 10 is of generally conventional construction and materials, preferably plastic includes a hollow barrel 12 having a central longitudinal axis A. The barrel has an inner surface 14 and is configured to hold an injectable liquid therein. A syringe or delivery conduit is located at the distal end of the barrel and is in fluid communication therewith. The plunger 26 is also of generally conventional construction and materials. A gasket 14 of the disclosure is attached to its distal end of the plunger.

Gasket Manufacturing and Laser Cut Process

In some embodiments of the present disclosure, the gasket comprises two materials: a bromobutyl rubber base gasket and a film, preferably a PTFE film, that resides on the outside surface. Examples of a bromobutyl rubber include: Sumitomo LAG 5010-50 and West 4023. The PTFE film in preferred embodiments substantially covers the outer surface of the gasket. Gasket manufacturing comprises the following processes, which pertain to some embodiments of this disclosure:

(a) Molding: The PTFE film is treated to promote adhesion with the bromobutyl rubber of the gasket. A typical treatment is corona treatment. In some embodiments, chemical treatments may also be used. The PTFE film is placed into a multi-cavity gasket mold. Bromobutyl rubber is poured/injected into the multi-cavity mold. The mold is closed, the PTFE film and bromobutyl rubber are formed into the gasket. The mold opens, and the gaskets are removed from the mold. The gaskets thus produced have a substantially uniform wall thickness and comprise rubber and PTFE. The gaskets are trimmed via die cutting to remove the excess material. In some embodiments, the multi-cavity mold produces gaskets which are not threaded within the internal cavity.

(b) Laser cut the PTFE or other film: The improved process of the disclosure comprises the following steps: (1) inserting a portion of one end of a mandrel into the open end of the gasket cavity of the gaskets manufactured in step (a); (2) securing the gasket to the mandrel; (3) positioning the mandrel and secured gasket in proximity to a laser; and (4) applying a laser beam emitted from a precision laser to one or more selected locations on a surface portion of the film residing on the circumferential outer surface portion of the gasket while rotating the mandrel and the secured gasket along the mandrel's longitudinal axis to produce one or more continuous channels in the film, the channels extending around the entire circumference of a circumferential outer surface of the gasket. This process produces one or more continuous channels in the PTFE or other film circumferentially on the outer surface of the gasket. The precision of the channels produced by the laser beam is directly related to the securing of the gasket on the mandrel, the position of the laser beam, and the dimensional tolerance of gaskets used in the process.

The resultant channel or channels creates a physical separation in the PTFE or other film on the gasket. In particular, without being bound by theory, it is believed that the laser treatment melts the PTFE or other film, and pushes the PTFE material to either side of the channel. During the laser treatment, the PTFE or other film material is 'piled' on either side of the channel creating two sealing ribs or peaks (micro projections). The PTFE or other film sealing ribs on either side of the channel are capable of maintaining CCI—both a liquid barrier and a sterile barrier. Assuming the PTFE film thickness is uniform and 'defect free', the height and angle of the sealing ribs, however, are dependent on the alignment and position control of the laser beam (relative to the rotating gasket on the mandrel). The greatest source of variation in the sealing ribs is due to the PTFE or other film: (1) variation in the thickness on the film and (2) defects in the film (ex. occlusions).

Moreover, fluoropolymer films are commonly stretched in the course of manufacture, when forming the initial film. This stretching process forms microchannels or micropores in the film (the terms "microchannel" or "micropore" are used interchangeably in this specification) which vary in size and dimensions depending on the specific manufacturing conditions. These microchannels or micropores are believed, at least in some instances, to provide a path along the fluoropolymer or other film from the back of the gasket of a prefilled syringe, which is outside the sealed portion of the syringe, into the lumen of the syringe containing the material filling the syringe. This reduces the CCI of the matched syringe-plunger system and reduces shelf life.

While cutting one or more channels in the film may alleviate some of the degradation of container closure integrity and lessened shelf life occasioned by these microchannels, the very process of producing the channels may also cause other problems that degrade CCI and shelf life. For example, without wishing to be bound by theory, unless the gasket is appropriately secured during the laser cutting process, it may sag on its outer surfaces or otherwise be deformed lending to inconsistencies and variations in the channels. Also, unless the gasket and channels are carefully and individually inspected after production, the failure rate of the gasket when used in syringe plunger systems will be unacceptable.

The improved process, gasket and syringe-plunger system of this disclosure overcomes those problems. Moreover, the rigorous inspection process of the disclosure ensures that the failure rate of the gaskets when used in syringe-plunger systems is low.

Improved gasket inspection system: The inspection of the gasket characteristics post gasket manufacture, and in some embodiments, post the laser treatment process of the present disclosure includes but is not limited to the following: (1) Dimensional checking of the overall height and outside diameter of the gasket; (2) Camera inspection of the shape of sealing ribs; (3) Camera inspection of the laser cut, e.g., verifying the peak and laser cut dimensions (peak height, peak width, axial width, laser cut depth, and radial depth (if present)); and (4) Camera inspection of the PTFE film for wrinkles, tears or evidence of debonding (lack of adhesion) to the rubber. Further tests to inspect the properties of the syringe and gasket systems of the present disclosure are also performed, e.g., container closure integrity testing (CCIT), plunger break loose and glide forces testing, sterility assurance and sub-visible particle testing.

Gasket Inspection (die cut and micro projection): A vision system is used to inspect the plungers in-line (100% inspection). One example of high speed inspection system for plunger is manufactured by Simac (Netherlands). The camera inspection system has the following attributes: (1) 13 plungers/sec; (2) Supports a wide range of plunger colors; (3) Performs top bottom, outside and inside surface inspection; (4) Inspects the micro-projection; (5) Inspects stamping and shape faults; (6) 100% quality control with a minimum defect detection of 100 μm. The rejected parts are categorized in separate containers and statistically traced. Good parts are exactly counted and automatically packed.

Dimensional Measure with Laser micrometer: Each completed gasket of the present disclosure is measured for dimensional consistency. Preferably, this is an in-line system. In a preferred embodiment, a scanning laser micrometer is used to perform these measurements. An example of a scanning laser micrometer is the LS-3000 series, manufactured by Keyence. A scanning laser micrometer uses a rotating optical element to reflect or refract a laser beam through a measurement area and across the path of an object to measure. The part obstructs the laser light, creating a shadow that persists for a time proportional to the size of the part. Optics in the receiver collect the unobstructed laser light and focus it on a photocell. The output of the photocell is analyzed by electronics to detect the precise time at which the laser crosses each part edge. Software converts timing data into meaningful measurements.

Sorting: Using the dimensional measurements, the gaskets of the present disclosure may be sorted to ensure that each gasket a specific dimensional tolerance. The tolerance can be ±100 micron, more specifically ±50 microns, more specifically ±35 microns, more specifically ±25 microns, more specifically ±20 microns, more specifically ±15 microns, more specifically ±10 microns, more specifically ±5 microns, more specifically ±3 microns.

The pre-filled syringe barrel dimensions are measured in a similar manner so that a precise and consistent fit between the syringe and the gasket is achieved. This enables precise control of gasket compression in the assembled syringe. The quality attributes of the assembled syringe include but are not limited to: (1) container closure integrity measure by dye ingression, (2) container closure integrity measure by vacuum decay method, (3) plunger force profile (Fi/Fm) consistency (aging and lot-to-lot variability).

In some embodiments, a lubricated gasket of the present disclosure maintains container closure integrity with a defect failure rate of at least 6-sigma. System elements may include: 100% inspection of molded plunger; 100% inspection of laser cut or channel of plunger fluoropolymer; 100% inspection of plunger diameter; 100% measurement of syringe barrel ID; and Low draft syringe barrel.

In some embodiments of the improved laser process of the present disclosure, there is 100% inspection of (a) the depth around the perimeter of the gasket secured on a stainless steel mandrel; (b) the shape of the film edges formed by the laser cut or channel using a servo motor to control the laser movement. In some embodiments, the adhesion of the film to the rubber gasket using plasma and/or chemical treatments is optimized.

Testing of container closure integrity (CCI) may be done using a vacuum decay leak detection method, wherein a vacuum is maintained inside of a test volume and pressure rise is measured over time. A large enough pressure rise is an indication that there is flow into the system, which is evidence of a leak. Optionally, the vacuum decay test is implemented over two separate cycles. The first cycle is dedicated to detecting large leaks over a very short duration. A relatively weak vacuum is pulled for the first cycle because if a gross leak is detected, a large pressure differential is not necessary to detect a large pressure rise. Use of a first cycle as described helps to shorten total test time if a gross leak exists. If no leak is detected in the first cycle, a second cycle is run, which complies with ASTM F2338-09 Standard Test Method for Nondestructive Detection of Leaks in Packages by Vacuum Decay Method. The second cycle starts out with a system evaluation to lower the signal to noise ratio in the pressure rise measurements. A relatively strong vacuum is pulled for a long period of time in the second cycle to increase the chance of detecting a pressure rise in the system.

EXAMPLES

Example 1: Liquid CCI Test Method

Syringe and gasket systems of the disclosure are filled with water and the stoppers are vacuum loaded. The syringes are stored needle-end up at 4° C. Each syringe is removed at specific time-points (0 days, 1 day, 4 days, 7 days, 1 month, and 3 months), allowed to reach room temperature, and then visually inspected for signs of water that has entered the space between the ribs of the stopper. A text description of each failure is recorded and a photo is taken of each failure. The leakage properties of the syringes of the present disclosure are compared with the leakage properties of other syringes with gasket films (such as a laminated film). The syringes of the present disclosure have superior CCI over time compared to syringes that were not produced by the improved laser and inspection process of the disclosure.

The invention claimed is:
1. A process for making one or more continuous channels in a film residing on at least a circumferential outer surface portion of a gasket, the gasket comprising a main body made of an elastic material, the main body having a circumferential surface portion and an internal cavity in its center, the cavity being defined by an inner surface portion of the gasket and being open at one end, the process comprising the following steps:
  (a) inserting a portion of one end of a mandrel into the open end of the cavity;
  (b) securing the gasket to the mandrel;
  (c) positioning the mandrel and secured gasket in proximity to a laser; and
  (d) applying a laser beam emitted from the laser to one or more selected locations on a surface portion of the film residing on the circumferential outer surface portion of the gasket while rotating the mandrel and the secured gasket along the mandrel's longitudinal axis to produce one or more continuous channels in the film, the channels extending around the entire circumference of a circumferential outer surface of the gasket.

2. The process of claim 1, wherein the thickness of the film on the surface of the gasket prior to step (d) is about 10-30 microns, about 15-35 microns, about 20-50 microns, or about 20 microns.

3. The process of claim 1, wherein the film has one or more of good slidability and chemical stability.

4. The process of claim 1, wherein the film is capable of preventing migration of components from the elastic material of the gasket.

5. The process of claim 1, wherein the gasket is secured to the mandrel by press-fit assembly.

6. The process of claim 1, wherein the diameter of at least a part of the mandrel portion that is inserted into the internal cavity of the gasket is greater than the inner diameter of the cavity.

7. The process of claim 1, wherein when more than one channel is produced, the channels are axially spaced.

8. The process of claim 1, wherein the one or more channels have axially opposed first and second side walls and a floor.

9. The process of claim 8, wherein the one or more channels each independently has one or more of:
   (a) an axial width between the side walls selected from 1-100 microns, 5-50 microns, 10-30 microns, and 15-25 microns;
   (b) a radial depth selected from 0-100 microns, 5-50 microns, 10-30 microns, and 15-25 microns; and
   (c) a laser-cut depth selected from 20-80 microns, 30-60 microns, 40-50 microns, 50-60 microns, 40-45 microns, 45-50 microns, 50-55 microns and 55-60 microns.

10. The process of claim 1, wherein the one or more channels extend through the film into the outer surface portion of the gasket.

11. The process of claim 1, wherein the one or more channels comprise a first circumferentially extending lip located adjacent to the first side wall of the channel and extending radially above the film and, optionally, a second circumferentially extending lip located adjacent to the second side wall and extending radially above the film.

12. The process of claim 11, wherein the first and second lips independently have a peak height selected from 10-100 microns, 15-60 microns, 20-50 microns, or 30-40 microns and a peak width selected from 200-1,000 micron, 275-550 microns, 300-400 microns, or 450-500 microns.

13. The process of claim 11, wherein each lip comprises film material displaced from the channel by the laser beam as the channel is produced.

14. The process of claim 13, wherein at least one lip is capable of being positioned in a tubular syringe barrel so as to form a seal against the inner surface of the barrel.

15. The process of claim 1, wherein the position of the laser relative to the mandrel and secured gasket is controlled by a servo-motor.

16. The process of claim 1, wherein the film is a fluoropolymer film.

17. The process of claim 15, wherein the fluoropolymer film is polytetrafluoroethylene (PTFE).

18. The process of claim 1, wherein the gasket is characterized by one or more of a dimensional tolerance selected from ±100 micron, ±50 microns, ±35 microns, ±25 microns, ±20 microns, ±15 microns, ±10 microns, ±5 microns, or ±3 microns; and fewer than 300 particles of 2 micron size or more, measured using light obscuration (LO) or microflow imaging (MFI).

* * * * *